(12) United States Patent
Tarabichi

(10) Patent No.: US 7,094,259 B2
(45) Date of Patent: Aug. 22, 2006

(54) PHYSIOLOGICAL TOTAL KNEE IMPLANT

(76) Inventor: Samih Tarabichi, P.O. Box 32238, Dubai (AE)

( * ) Notice: Subject to any disclaimer, the term of this patent is extended or adjusted under 35 U.S.C. 154(b) by 0 days.

(21) Appl. No.: 10/626,400

(22) Filed: Jul. 24, 2003

(65) Prior Publication Data
US 2005/0021147 A1 Jan. 27, 2005

(51) Int. Cl.
A61F 2/38 (2006.01)

(52) U.S. Cl. .................................. 623/20.14; 623/20.33
(58) Field of Classification Search .... 623/20.14–20.34
See application file for complete search history.

(56) References Cited

U.S. PATENT DOCUMENTS 5,395,401 A * 3/1995 Bahler ..................... 623/20.29
6,500,208 B1 * 12/2002 Metzger et al. .......... 623/20.28
6,620,198 B1 * 9/2003 Burstein et al. .......... 623/20.28

OTHER PUBLICATIONS

S. Nakagawa, Y. Kadoya, S. Todo, A. Kobaysashi, H. Sakamoto, M.A.R. Freeman, Y. Yamano; Tibio–femoral, movement 3: full flexion in the living knee studied by MRI; The Journal of Bone & Joint Surgery (Br); vol. 82–B, No. 8, Nov. 2000.

Peter S. Walker, PHD, Richard D. Komistek, PHD, David S. Barrett, FRCS, Dylan Anderson, BS, Douglas A. Dennis, MD Andmadeleine Sampson, FRCR, FRCP; Motion of a Mobile Bearing Knee Allowing Translation and Rotation; The Journal of Arthroplasty, vol. 17, No. 1 2002.

* cited by examiner

Primary Examiner—David J. Isabella
(74) Attorney, Agent, or Firm—Adams and Reese LLP

(57) ABSTRACT

The present invention generally comprises a fixed bearing prosthesis and a mobile bearing prosthesis. The fixed bearing prosthesis comprises a tibial component, a femoral component and a meniscal component and addressees the loss of congruency during deep knee flexion and the possible direct, repetitive contact of the tibial and femoral components. The tibial component of the fixed bearing prosthesis includes a tibial platform having an anterior and posterior edge. The meniscal component of the fixed bearing prosthesis includes a posterior ridge overlapping the posterior edge of the tibial platform that prevents metal-to-metal contact during deep knee flexion. The mobile bearing prosthesis comprises generally a tibial component, a femoral component and a meniscal component addresses the lack of conformity to natural biomechanical movement. The tibial component comprises a tibial platform having a curved rail system designed to mimic the asymmetrical rotation of femoral rollback while simultaneously providing sufficient anterior-posterior translation.

3 Claims, 4 Drawing Sheets

Prior Art

PHYSIOLOGICAL TOTAL KNEE IMPLANT

STATEMENT REGARDING FEDERALLY SPONSORED RESEARCH OR DEVELOPMENT

Not Applicable

FIELD OF THE INVENTION

The present invention relates to total knee arthroplasty and, more particularly to an improved meniscal component for both fixed bearing and mobile bearing prostheses.

BACKGROUND OF THE INVENTION

Total knee prostheses can be divided into two general categories: fixed bearing and mobile bearing. Both the fixed and mobile bearing knee prosthesis includes a femoral component, a tibial component, and a meniscal component, or bearing, which is located between the femoral component and the tibial component. In the conventional fixed bearing prosthesis, the bearing is fixedly attached to the tibial component. In the conventional mobile bearing prosthesis, the bearing is allowed some limited range of symmetrical motion. The form of the prosthetic knee joint selected by the orthopedic surgeon depends upon the condition of the natural knee and the age, health and mobility of the patient.

Fixed bearing prostheses are generally indicated where there is severe damage to the femur and/or tibia or when neither the posterior nor anterior cruciate ligaments can be retained. The fixed bearing prosthesis generally does not allow correction for a misplacement in rotation on the tibial component and may contribute to accelerated wear of the bearing component due to high contact stresses. Congruency between the femoral and tibial articulating surfaces must be balanced to provide maximum contact area, which lowers the stresses on the bearing without constraining the normal movement of the femur on the tibia, which could result in high shear stress. During deep knee flexion, congruency may be lost resulting in direct, repetitive contact between the femoral and tibial components. Prior art fixed bearing prostheses have not addressed this concern.

Mobile bearing prostheses were developed in an effort to replicate the normal biomechanics of the natural knee joint and are generally indicated for patients who have adequate collateral ligament stability. Many prior art mobile bearing prostheses are limited to a simple rotation, which in some instances is coupled with constrained anterior-posterior translation. In these systems, the displacement of the lateral portion of the bearing component about the axis of rotation is generally symmetrical, which causes the femoral component to strike and erode the bearing component due to the asymmetrical characteristic of femoral rollback. Other prior art mobile bearing prostheses are limited to anterior-posterior translation in the absence of rotational misalignment correction, thus do not conform to natural biomechanical movement.

Accordingly, a fixed bearing prosthesis and a mobile bearing prosthesis are disclosed. The fixed bearing prosthesis comprises generally a tibial component, a femoral component and a meniscal component disposed between the tibial and femoral components and addressees the loss of congruency during deep knee flexion and the possible direct, repetitive contact of the tibial and femoral components. The tibial component of the fixed bearing prosthesis includes a tibial platform having an anterior and posterior edge. The meniscal component of the fixed bearing prosthesis includes a posterior ridge overlapping the posterior edge of the tibial platform that prevents metal-to-metal contact during deep knee flexion. The mobile bearing prosthesis comprises generally a tibial component, a femoral component and a meniscal component disposed between the tibial and femoral components and addresses the lack of conformity to natural biomechanical movement. The tibial component comprises a tibial platform having a curved rail system designed to mimic the asymmetrical rotation of femoral rollback while simultaneously providing sufficient anterior-posterior translation.

PREFERRED EMBODIMENTS OF THE INVENTION

Figure 1:
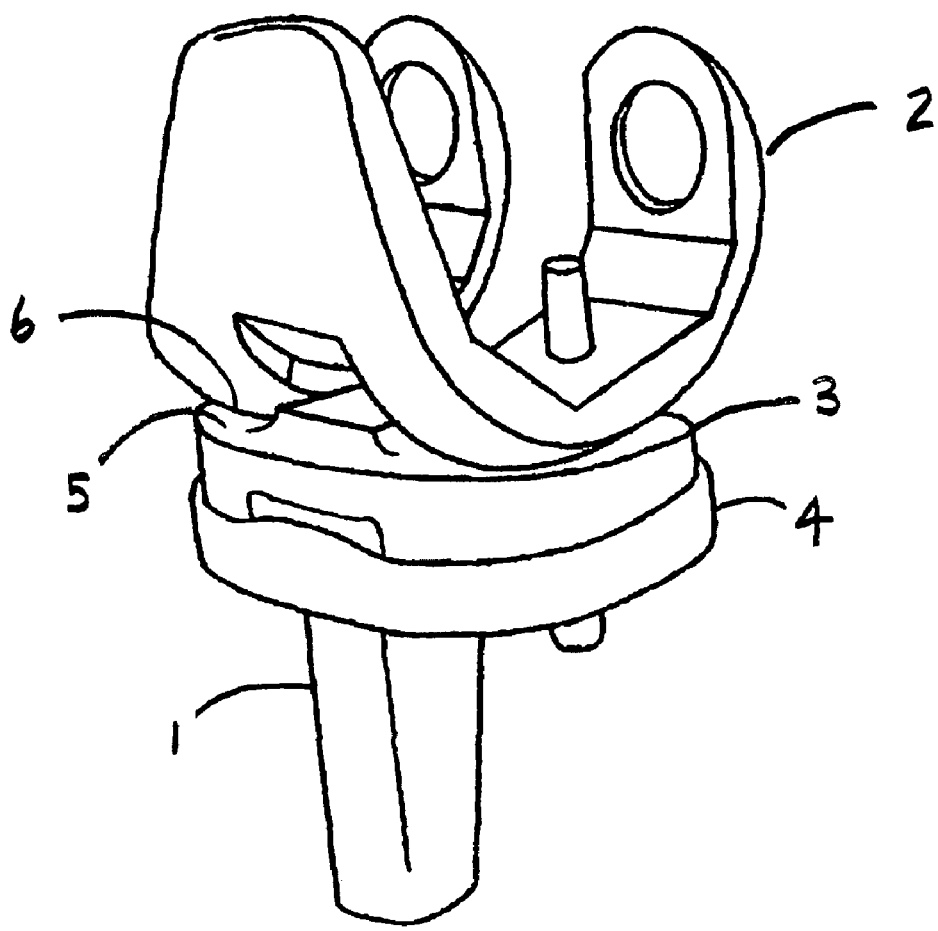
FIG. 1 illustrates a conventional fixed bearing prosthesis.

In the following detailed description of the preferred embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Movement of the natural knee joint can be classified as having 6 degrees of freedom: three translations, including anterior/posterior, medial/lateral, and inferior/superior; and three rotations, including flexion/extension, internal/external, and adduction/adduction. Movements of the knee joint are determined by the shape of the articulating surfaces of the tibia and femur and the orientation of the four major ligaments of the knee joint, including the anterior and posterior cruciate ligaments and the medial and lateral collateral ligaments.

Knee flexion/extension involves a combination of rolling and sliding called femoral rollback. Because of asymmetry between the lateral and medial femoral condyles, the lateral condyle rolls a greater distance than the medial condyle during knee flexion. This causes coupled external rotation of the tibia, which has been described as the "screw-home" mechanism of the knee that locks the knee into extension. During deep knee flexion, the lateral femoral condyle may roll back sufficiently to loose contact with tibia, a phenomena known as condylar liftoff.

As stated above, the orientation of the four major ligaments in the knee play a role in determining movement of the joint. The primary function of the medial collateral ligament is to restrain valgus rotation of the knee joint, with its secondary function being control of external rotation. The lateral collateral ligament restrains varus rotation and resists internal rotation.

The primary function of the anterior cruciate ligament is to resist anterior displacement of the tibia on the femur when the knee is flexed and control the "screw-home" mechanism of the tibia in terminal extension of the knee. A secondary function of the anterior cruciate ligament is to resist varus or valgus rotation of the tibia, especially in the absence of collateral ligaments. The anterior cruciate ligament also resists internal rotation of the tibia.

The primary function of the posterior cruciate ligament is to allow femoral rollback in flexion and resist posterior translation of the tibia relative to the femur. The posterior cruciate ligament also controls external rotation of the tibia with increasing knee flexion.

The natural knee joint can become damaged or diseased such that the articular surfaces of the femur or tibia may deteriorate and cause damage to the articular cartilage between the bones. In these instances, total knee arthroplasty is often indicated. However, knee replacement has a finite expected survival that is adversely affected by activity level. Thus, significant research and development has been directed to the development of knee prostheses that minimize the possibility of dislocation, bearing failure and loosening from the bones, and that significantly imitates the natural motion of the knee joint.

The design of any total knee replacement must provide appropriate joint function and range of motion, transfer the large loads that cross the joint from the implant components to the surrounding bone, and allow for long-term use without severe wear to the implant surfaces. In addition to selecting the appropriate design, the surgeon must also determine whether to sacrifice or retain the posterior cruciate ligament.

Fixed bearing prostheses meet these design requirements by having bicondylar geometries with curved surfaces in both the anteroposterior and medial-lateral directions. The appropriate choice of radii of curvatures for the tibial and femoral components minimizes contact stresses, while providing adequate restraint. In the instances when the posterior cruciate ligament is sacrificed, the prosthesis typically incorporates a femoral cam and tibial spine to control femoral rollback and prevent anterior sliding and posterior subluxation of the knee.

On the other hand, mobile bearing prostheses allow for more natural joint kinematics, while also allowing the articulating surfaces to be more conforming than a fixed-bearing knee, leading to larger contact areas, lower contact stresses, and better wear resistance.

As shown in FIG. 1, conventional fixed bearing prostheses generally comprise a tibial component 1, a femoral component 2 and a meniscal component 3 disposed between the tibial component 1 and femoral component 2. The meniscal component 3 is locked into the tibial component 1 and does not move from the tibial tray 4. The meniscal component 3 provides a surface 5 where the articular surface 6 of the femoral component 2 can slide without any significant friction.

Figure 2:
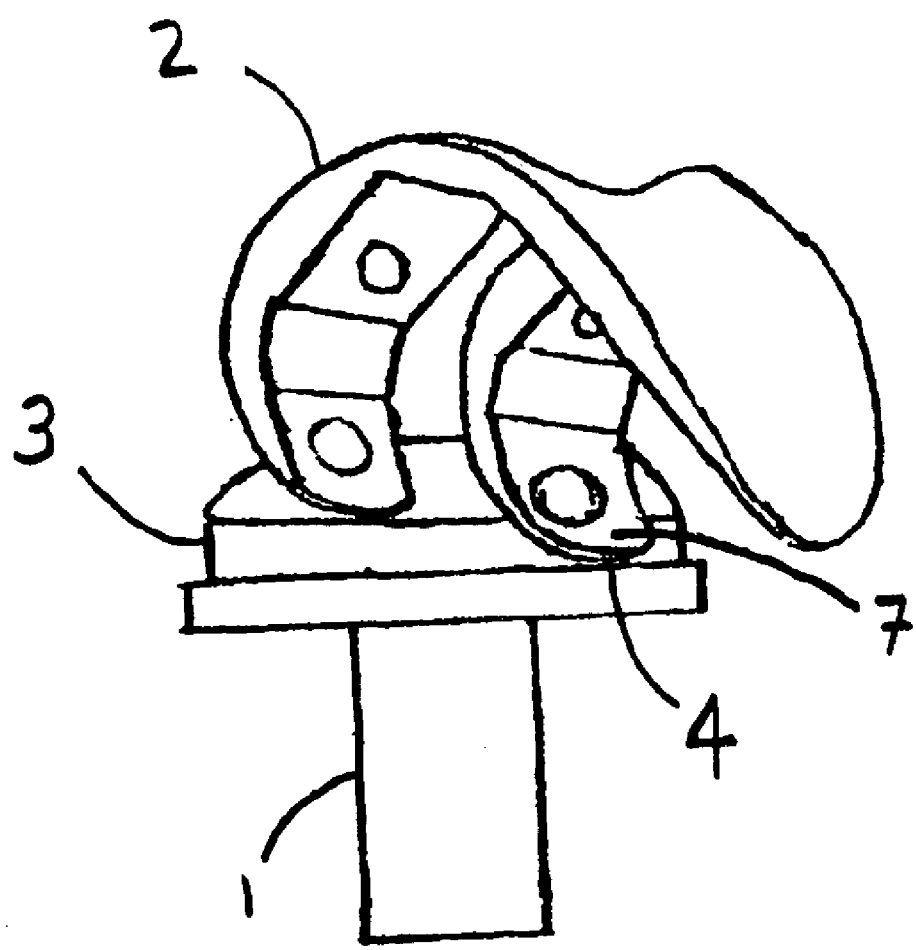
FIG. 2 illustrates condylar liftoff with a conventional fixed bearing prosthesis and the possibility of direct metal-to-metal contact between the femoral and tibial components.

FIG. 2 illustrates condylar liftoff during deep knee flexion. The lateral condyle 7 of the femoral component 2 lifts off of the meniscal component 3 during femoral rollback. With deep knee flexion, the metal surface of lateral condyle 7 may come into direct and repetitive contact with the metal surface of the tibial tray 4 of the tibial component 1.

Figure 3A:
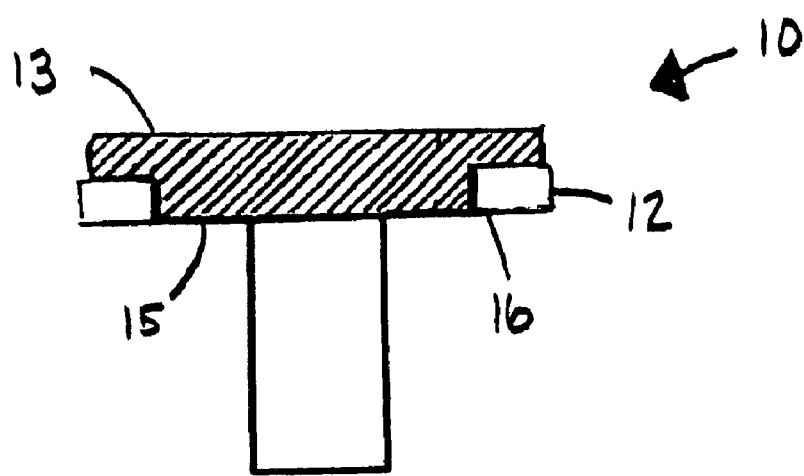
FIG. 3a is a rear perspective view of one preferred embodiment of a fixed bearing prosthesis featuring an improved meniscal component.
Figure 3B:
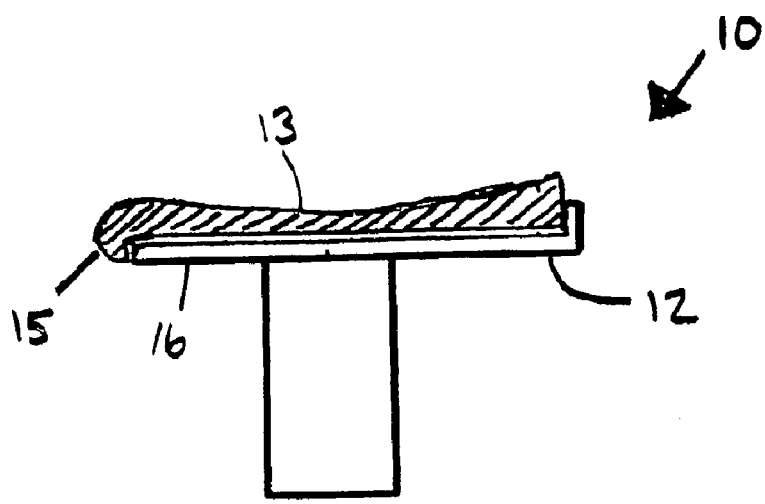
FIG. 3b is a side perspective view of one preferred embodiment of a fixed bearing prosthesis featuring an improved meniscal component.

FIGS. 3a and 3b show one preferred embodiment of a fixed bearing prosthesis of the present invention that addresses the potential metal-to-metal contact between the lateral condyle 7 of the femoral component 2 and the tibial tray 4. As seen in FIG. 3a, the tibial component 10 of the fixed bearing prosthesis comprises a tibial tray 12 and a fixed bearing 13 that is fixedly attached to the tibial tray 12. The fixed bearing 13 comprises a posterior ridge 15 that overlaps the posterior edge 16 the tibial tray 12. FIG. 3b shows the same fixed bearing prosthesis in a side perspective view.

The femoral component and the tibial components of the fixed bearing prosthesis of the present invention may be made of any conventional biocompatible material, including but not limited to, titanium, titanium alloy, cobalt-chrome, alumina or zirconia ceramic. The femoral and tibial components may be fixed by cement, a hydroxyaptite coating, or by any other conventional means.

The shape of the meniscal component, the fixed bearing, has a generally planar inferior surface with a generally downward extending posterior ridge that overlaps the posterior edge of the tibial tray. The superior surface of the meniscal component may include one or more generally concave depressions to match the generally convex surfaces of the condylar portions of the femoral component. The meniscal component may be made of any conventional biocompatible material, however, ultra high molecular weight polyethylene is typically employed.

Mobile bearing knee prostheses reduce meniscal component wear and mimic the normal biomechanics of the natural knee joint. The mobile bearing prosthesis of the present invention is not limited to a simple rotation. The meniscal component is allowed to slide along curved rail that forces the knee to follow a more normal physiological pattern as opposed to conventional designs. The radius of the curved rail allows the femoral condyle to rotate and slide on the tibial plateau imitating the physiological movement of the knee.

Figure 4:
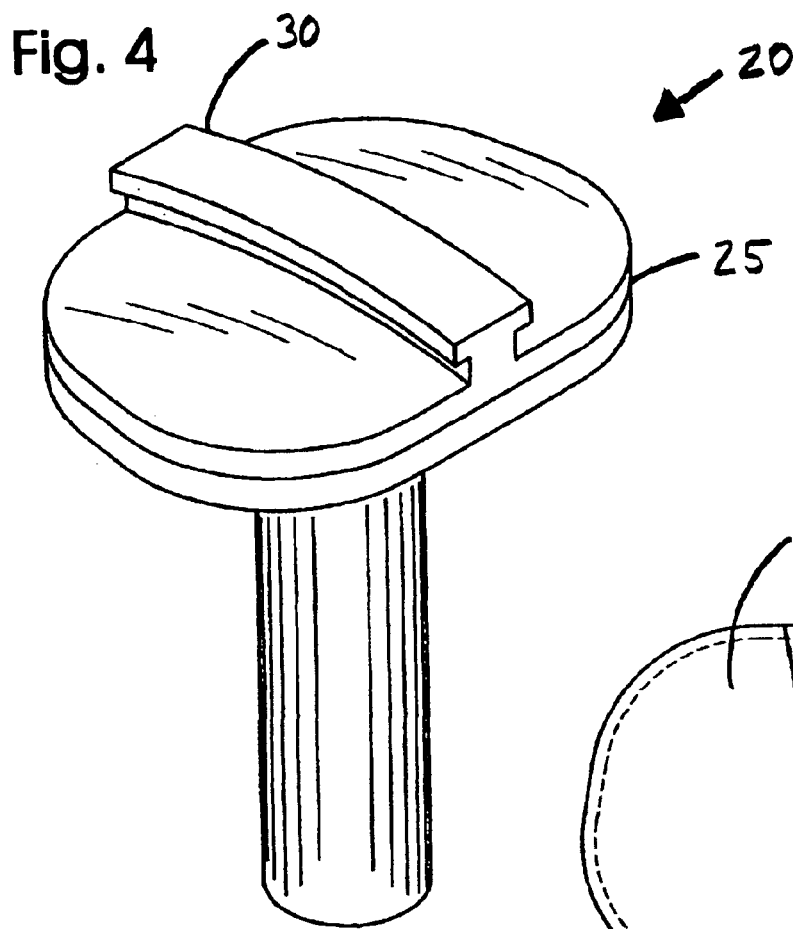
FIG. 4 is a side perspective view of the tibial component of one preferred embodiment of a mobile bearing prosthesis in accordance with the present invention.
Figure 5:
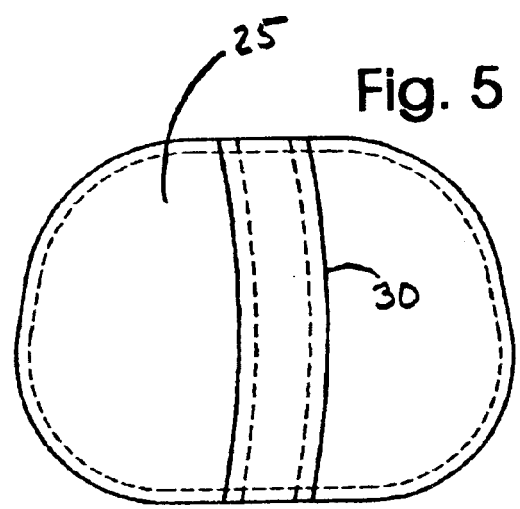
FIG. 5 is a top perspective view of the tibial component shown in FIG. 4.

FIG. 4 illustrates the tibial component 20 of one preferred embodiment of a mobile bearing prosthesis of the present invention. The tibial component 20 generally comprises a tibial platform 25 having a curved rail 30 designed to mimic the asymmetrical rotation of femoral rollback while simultaneously providing sufficient anterior-posterior translation. The shape of curved rail 30 may conform to any conventional rail design, such as a dovetail or T-shaped rail. However, the preferred shape of curved rail 30 is a T-shape rail. FIG. 5 is a top perspective view of tibial component 20 illustrating the curvature of T-shape rail 30. The tibial platform 25 may be integrally constructed as a monolithic tibial component, or the tibial platform may be fixedly attached to the tibial component 20 by conventional means.

Figure 6:
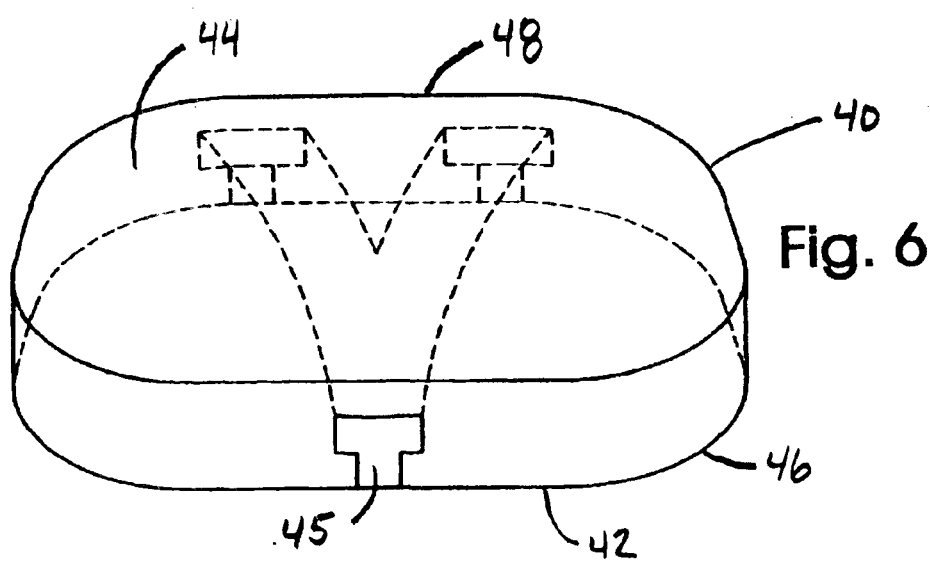
FIG. 6 is a front perspective view of the meniscal component of one preferred embodiment of a mobile bearing prosthesis in accordance with the present invention.

The mobile meniscal component 40 is shown in FIG. 6. The mobile meniscal component 40 comprises a generally planar inferior surface 42 and a superior surface 44. The inferior surface 42 comprises a keyway 45 that slidingly accepts the T-shaped curved rail 30 of the tibial platform 25. The keyway 45 extends from the anterior edge 46 of meniscal component 40 to the posterior edge 48. The curvature of the keyway 45 is substantially similar to the curvature of the T-shaped rail 30 such that during deep knee flexion, the meniscal component 40 slides along the T-shaped rail 30 allowing for asymmetrical rotation as well as anterior-posterior translation. As with the fixed bearing design, the superior surface of the meniscal component may include one or more generally concave depressions to match the generally convex surfaces of the condylar portions of the femoral component and may be made of any conventional biocompatible material, however, ultra high molecular weight polyethylene is typically employed. The meniscal component 40, as seen in FIG. 6, may employ a branched keyway, which would allow the same meniscal component 40 to be used for either right or left knee arthroplasty.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A mobile bearing prosthesis for total knee arthroplasty comprising: a femoral component; a tibial component having a superior tibial platform, said superior tibial platform having an anterior edge, a posterior edge, and an arcuate rail projecting upward from said superior tibial platform, said arcuate rail extending from said anterior edge of said superior tibial platform to said posterior edge of said superior tibial platform; and a meniscal component, having an inferior meniscal surface, a superior meniscal surface, an anterior meniscal edge and a posterior meniscal edge, said inferior meniscal surface having a keyway extending from said anterior meniscal edge to said posterior meniscal edge, said keyway slidingly attached to said arcuate rail and and said keyway comprising a symmetrical y-shape branch, the tail portion of said y-shaped branched keyway located on said way located on said anterior meniscal edge of said meniscal component and the branched portion of said y-shaped branched keyway located on said posterior meniscal edge of said meniscal component, said y-shaped branched keyway allowing said maniscal component to be used for left knee arthroplasty and right knee arthroplasty.

2. The mobile bearing prosthesis of claim 1, wherein said femoral component further comprises one of more condylar portions having substantially convex surfaces and said superior meniscal surface further comprises one or more substantially concave depressions in sliding communication with said substantially convex surfaces of said one or more condylar portions of said femoral component.

3. The mobile bearing prosthesis of claim 1, wherein said arcuate rail on said superior tibial platform and said keyway on said inferior meniscal surface have a t-shaped cross-section.

* * * * *